United States Patent [19]

Chen

[11] Patent Number: 5,699,556

[45] Date of Patent: Dec. 23, 1997

[54] CATCHER'S FACE MASK WITH A SUN-SHADE

[75] Inventor: Shen-fa Chen, Taipei Hsien, Taiwan

[73] Assignee: Hun-yuan Chen, Taiwan

[21] Appl. No.: 718,896

[22] Filed: Sep. 24, 1996

[51] Int. Cl.⁶ .................................................. A61F 9/04
[52] U.S. Cl. .................................................... 2/9
[58] Field of Search ............................... 2/9, 425, 424, 2/12, 441

[56] References Cited

U.S. PATENT DOCUMENTS

| D. 333,536 | 2/1993 | Dooley ................................ D29/16 |
| D. 334,084 | 3/1993 | Hunt et al. .......................... D29/17 |
| 861,170 | 7/1907 | Gamble et al. ....................... 2/9 |
| 881,957 | 3/1908 | Ridlon ................................. 2/9 |
| 4,736,466 | 4/1988 | Kallstrom ............................ 2/9 |

Primary Examiner—Michael A. Neas
Attorney, Agent, or Firm—Sixbey, Friedman, Leedom & Ferguson; Stuart J. Friedman

[57] ABSTRACT

A catcher's face mask which has a sun-shade to shield a catcher' eyes from bright light from in front and from above. The catcher's face mask sun-shade includes a cage constructed to protect a catcher's face from a flying ball, and a lower padding attached to a lower inside portion of the cage by adhesive bands thereof and an upper padding attached to an upper inside portion of the cage by adhesive bands thereof at regular interval. A sun-shade having a glare-reducing strip with a curved bar affixed to a top surface thereof and a plurality of openings defined in the glare-reducing strip adjacent to the bar is provided in front of the upper padding but behind the cage, and secured to the cage by the bands of the upper padding extending through the respective openings and tightly adhering to a corresponding portion of the cage.

7 Claims, 4 Drawing Sheets

CATCHER'S FACE MASK WITH A SUN-SHADE

THE FIELD OF THE INVENTION

This invention relates a catcher's face mask, particularly, to a catcher's face mask having a sun-shade to shield a catcher's eyes from bright light from in front and from above.

THE BACKGROUND OF THE INVENTION

Baseball is one of the most popular and exciting games in the world. One important outfit of that game is a conventional face mask for a catcher and that mask is typically provided with a cage 40 constructed with curved bars in such a way that it can protect a catcher's face from a fly ball, with a lower 60 and an upper 70 paddings attached respectively to lower and upper inside portions of the cage 40 by adhesive bands 50, as shown in FIG. 4, so as to produce a cushioning effect on his face against the impact of a ball on the mask.

However, a catcher with such a face mask on may fail to follow the movement of a flying ball precisely with his eyes and subsequently not catch it properly, and in the worst case, may be badly hurt by the ball hitting at his body, since such a mask is so open that the catcher may be dazzled when the sun is shinning brightly in front of or above him.

SUMMERY OF THE INVENTION

It is an object of the present invention to provide a face mask which can shield a catcher' eyes from bright light from in front and from above.

To achieve the above object of the present invention, there is provided a catcher's face mask with a sun-shade wherein the mask includes a cage constructed to protect a catcher's face from a flying ball, and a lower padding attached to a lower inside portion of the cage by adhesive bands thereof and an upper padding attached to an upper inside portion of the cage by adhesive bands thereof at regular intervals. A sun-shade having a glare reducing strip, a curved bar affixed to a top surface thereof and a plurality of openings defined therein adjacent to the bar is provided in front of the upper padding but behind the cage, and secured to the cage by the bands of the upper padding extending through the respective openings and tightly adhering to a corresponding portion of the cage.

Other object of this invention will be more apparent from the descriptions which follow.

BRIEF DESCRIPTIONS OF THE DRAWINGS

DETAILED DESCRIPTION OF THE PREFERRED EMBODIMENT

Figure 1:
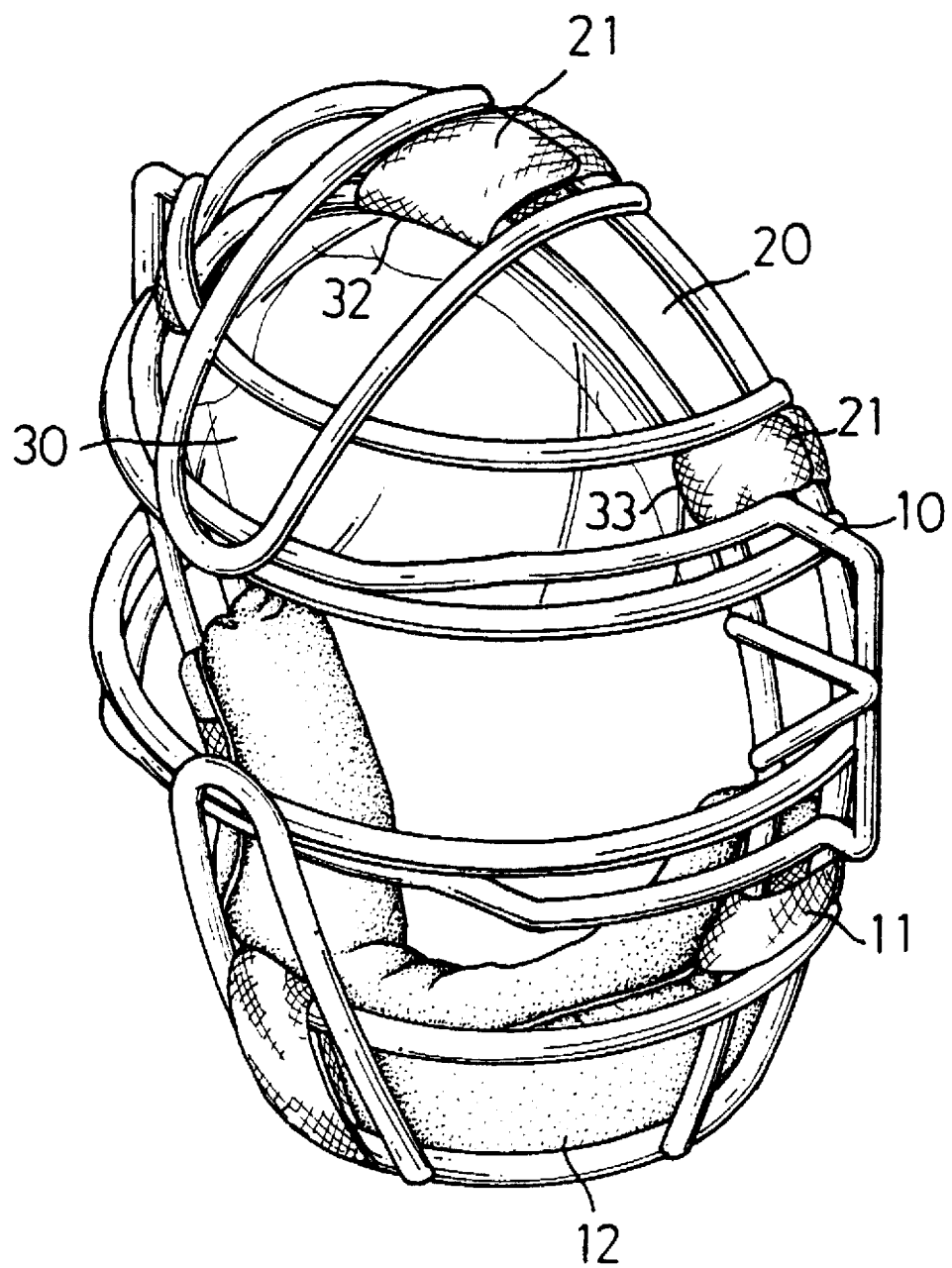
FIG. 1 is a perspective view of a face mask, in accordance with this invention.
Figure 2:
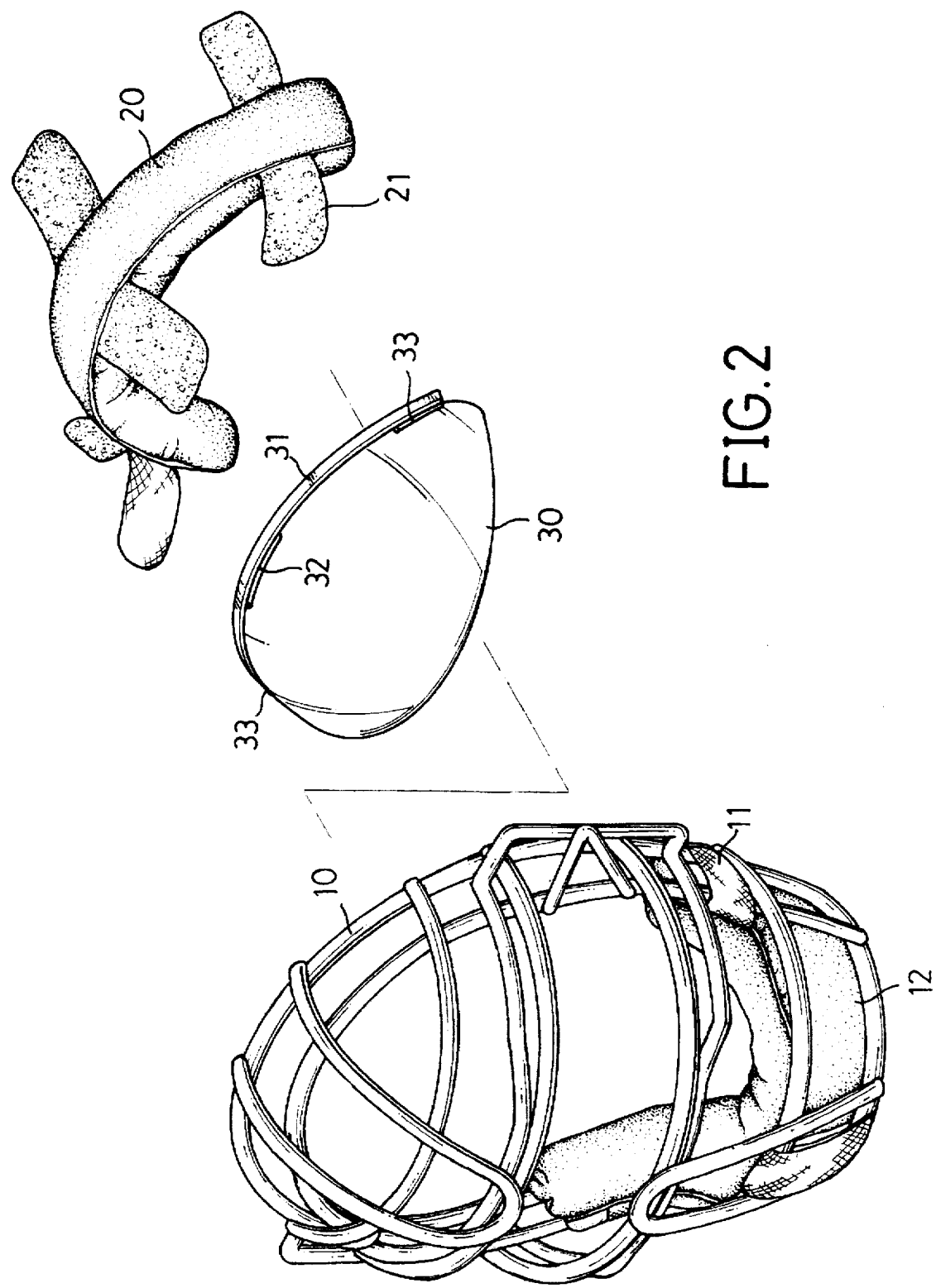
FIG. 2 is an exploded view of the face mask of FIG. 1.

In FIGS. 1 and 2 there is shown an inventive face mask including a cage 10 configured to protect a catcher's face from a flying ball, with a lower padding 12 and an upper padding 20 attached to a lower and an upper inside portion of the cage 10 respectively, by adhesive bands 11 and 21.

Figure 3:
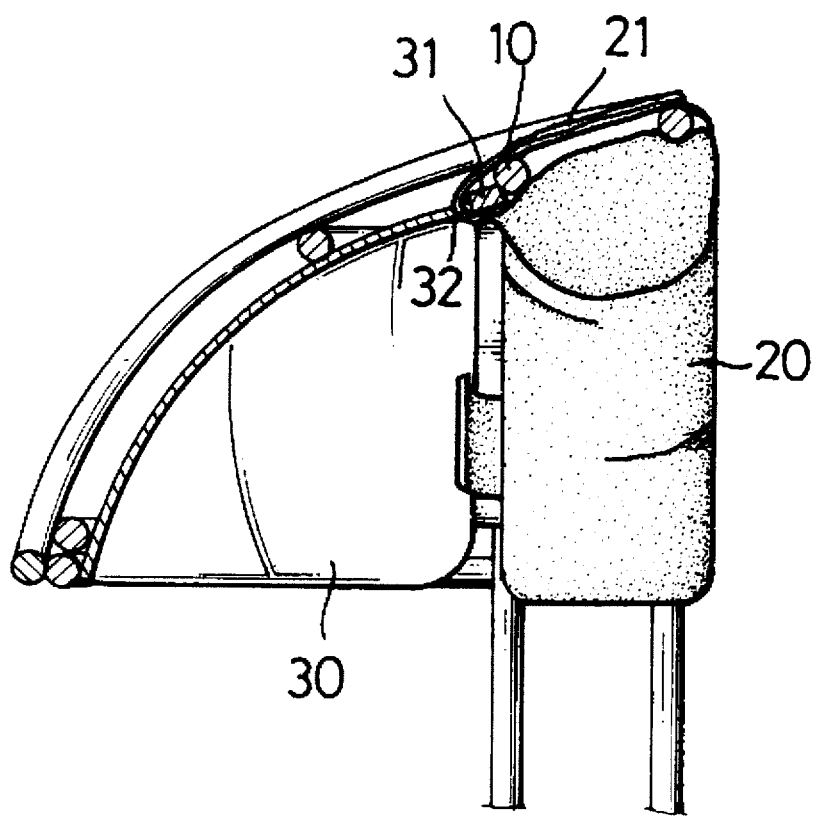
FIG. 3 is an enlarged view, partly in section, of FIG. 1 in assembly.
Figure 4:
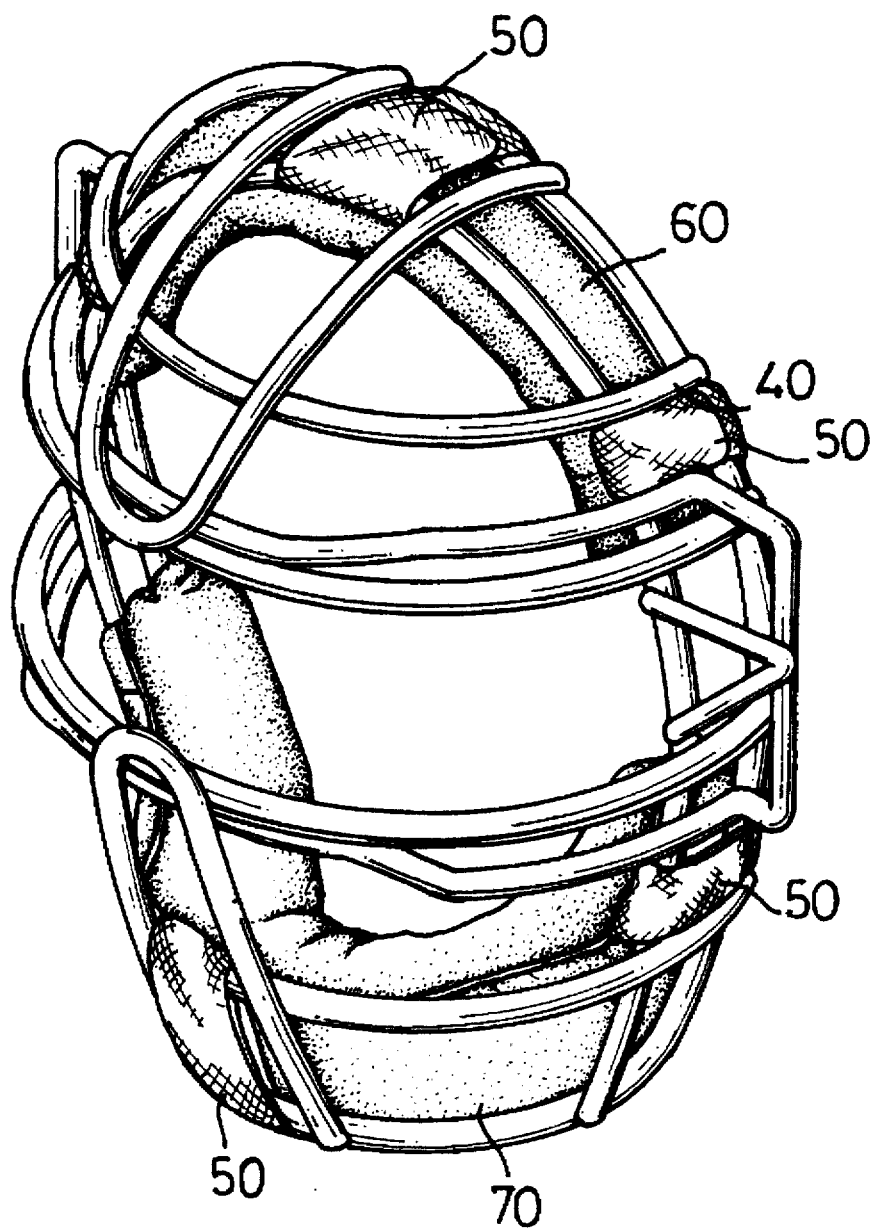
FIG. 4 shows a conventional face mask.

The face mask is characterized by the fact that a sun-shade 30, which comprises a glare-reducing strip, a curved bar 31 affixed to a top surface thereof and a plurality of openings 32 defined in the glare-reducing strip and adjacent to the bar 31, is provided in front of the upper padding 20 and behind the cage 10 by means of the bands 21 of the upper padding 20 which extends through the respective openings 32 and 33 of the sun-shade 30 and tightly adheres to a corresponding portion of the cage 10, as shown in FIG. 1 and best seen in FIG. 3.

Referring back again to FIG. 1, the provision of the sun-shade in such an arrangement as above-mentioned may shield a catcher' eyes from bright sun light from in front and from above, allowing him to have a good sight at a flying ball without the possibility of being hit by it.

While the principles of this invention have been described in connection with its embodiment, it should be understood that many other possible modifications and variations can be made without departing from the spirit and scope of the invention as hereinafter claimed.

What is claimed is:

1. In a catcher's face mask comprising a cage constructed to allow a catcher to see therethrough and protect the catcher's face from a flying ball, a lower padding attached to a lower inside portion of the cage, an upper padding attached to an upper inner portion of the cage, a sun-shade comprising a glare reducing strip having a plurality of openings defined therein and means for securing the sun-shade to the cage, the improvement comprising:

said openings are defined in one side edge of the sun-shade and a curved bar portion is affixed to said side edge of the sun-shade adjacent to said openings for forming a portion of the periphery of said openings.

2. A catcher's face mask, as claimed in claim 1, wherein said curved bar portion has a length which is less than the length of said side edge.

3. A catcher's face mask, as claimed in claim 1, wherein said means securing said sun-shade to said cage comprises bands passing through said openings and engaging a portion of said cage.

4. A catcher's face mask, as claimed in claim 3, wherein said bands form a part of said upper padding.

5. A catcher's face mask, as claimed in claim 4, wherein each said band includes at least one adhesive portion for overlapping engagement with another portion of said band.

6. A catcher's face mask, as claimed in claim 5, wherein said bands tightly adhere to said cage.

7. A catcher's face mask, as claimed in claim 4, wherein said bands extend from said upper padding, through said openings and around said curved bar portion.

* * * * *